United States Patent [19]

Mund et al.

[11] Patent Number: 4,779,618

[45] Date of Patent: Oct. 25, 1988

[54] DEVICE AND METHOD FOR THE PHYSIOLOGICAL FREQUENCY CONTROL OF A HEART PACEMAKER EQUIPPED WITH A STIMULATING ELECTRODE

[75] Inventors: Konrad Mund, Uttenreuth; Raghavendra Rao; Gerhard Richter, both of Erlangen, all of Fed. Rep. of Germany

[73] Assignee: Siemens Aktiengesellschaft, Berlin and Munich, Fed. Rep. of Germany

[21] Appl. No.: 764,850

[22] Filed: Aug. 12, 1985

[30] Foreign Application Priority Data

Aug. 10, 1984 [DE] Fed. Rep. of Germany ....... 3429596

[51] Int. Cl.⁴ .............................................. A61M 1/36
[52] U.S. Cl. ............................................. 128/419 PG
[58] Field of Search ............ 128/419 PG, 419 P, 635, 128/784–786

[56] References Cited

U.S. PATENT DOCUMENTS

| | | | |
|---|---|---|---|
| 2,913,386 | 11/1959 | Clark | 128/419 PG |
| 3,614,954 | 10/1971 | Mirowski et al. | 128/784 |
| 4,202,339 | 5/1980 | Wirtzfeld | 128/419 PG |
| 4,467,807 | 8/1984 | Bornzin | 128/419 PG |
| 4,467,896 | 8/1984 | Bornzin | 128/419 PG |
| 4,499,901 | 2/1985 | Chang et al. | 128/635 |
| 4,549,548 | 10/1985 | Wittkampf et al. | 128/419 PG |
| 4,611,604 | 9/1986 | Botvidsson et al. | 128/419 P |

OTHER PUBLICATIONS

Electrical Properties of Glassy-Carbon Electrodes; Med. & Biol. Eng. & Comput., 1979, 17, 465–470; Matsumoto.

Primary Examiner—William E. Kamm
Attorney, Agent, or Firm—Kenyon & Kenyon

[57] ABSTRACT

Physiological frequency control of a heart pacemaker having a stimulating electrode is accomplished by providing an oxygen measuring electrode and placing it in the body tissue, loading the oxygen measuring electrode with stimulating pulses in parallel with the stimulating electrode, measuring the potential of the oxygen measuring electrode relative to another electrode between stimulating pulses, and controlling the frequency of the pacemaker as a function of the measured potential.

10 Claims, 4 Drawing Sheets

DEVICE AND METHOD FOR THE PHYSIOLOGICAL FREQUENCY CONTROL OF A HEART PACEMAKER EQUIPPED WITH A STIMULATING ELECTRODE

BACKGROUND OF THE INVENTION

This invention relates to a device and a method for the physiological frequency control of a heart pacemaker equipped with a stimulating electrode by means of a control unit as well as to a method for operating such a device.

The most common applications of pacemaker therapy are the permanent and the temporary electrostimulation of the heart. On occassion, a combination of both methods may be necessary in cases which cannot be judged unequivocally. Permanent electrostimulation of the heart is used if Adams-Strokes attacks occur or in the event of total AV block (AV=atrioventricular node). In cases of bradycardic heart arrhythmia, temporary electrostimulation of the heart must be provided so that the physical capacity of the patient is improved.

For the permanent electrostimulation of the heart, heart pacemakers are known which contain a fixed frequency generator which delivers, for instance, 70 current pulses per minute at a constant rate. These heart pacemakers are of simple design and have a long service life even with standard chemical batteries. Such heart pacemakers can be used particularly for older people for whom a heart time-volume on the basis of 70 beats per minute is sufficient for their still tolerable extent of physical stress. In addition, the rhythm of the patient's heart itself is suppressed at least approximately. If spontaneous actions by the patient occur from one or several automation centers, the parasystolic behavior can lead not only to an irregular beat sequence with bunched occurrence of disturbed pacemaker pulses; it also can trigger, in particular, tachycardic states all the way to chamber fibrillation if the artificial stimuli fall into the valnerable phase, i.e., the T-wave of the intrinsic preceding action.

In addition, different types of so-called demand pacemakers are known. In demand sets, the pulse of the heart pacemaker is inhibited via an electrode located in the ventricle by the potential of the R-spike of the intrinsic actions as long as its frequency is above, for instance, 70 beats per minute. If it drops below this value, the device is switched on automatically and takes over the stimulation. In the "stand-by-pacer," the R-spike of the intrinsic rhythm acts, via the electrode, as a trigger pulse, to which the pacemaker is subordinated in the frequency range, for instance, of between 70 and 150 beats per minute with matched signal lapse. If intrinsic pulses are missing or if the R-spike spacings are smaller than between 300 and 400 msec, artificial stimulation is applied. If, however, the latter exceeds an upper predetermined pulse per minute value of, for instance, 150, the heart pacemaker cuts the frequency in half, i.e., it takes over the electrical stimulation of the heart with a correspondingly reduced pulse delivery. With these two types of demand pacemakers, the parasystolic state is avoided and an orderly side by side arrangement of the internal rhythm and artifical stimulation is obtained.

Furthermore, an electrochemical device for determining the oxygen content of a liquid is known. The measuring cell of this device consists of a tubular body in which a cathode and an anode are arranged in an electrolyte. The one end face of the measuring cell is provided with a diaphragm which is fastened by a sealing ring and a cap provided with an opening. This diaphragm separates the liquid to be examined from the electrode arrangement. The measurement principle consists of the electrochemical reduction of oxygen ($O_2$) where an oxygen diffusion limiting current is brought about at the electrode through the diaphragm. Thereby a measuring signal proportional to the concentration if obtained (U.S. Pat. No. 2,913,386). With a measuring cell of such a design, the oxygen concentration in the blood or tissue can be measured in vivo, however, only for a short time, for instance, for several days since the measuring cell becomes surrounded by developing connective tissue layers, and the measuring signal is thereby falsified.

It is, thus, an object of the present invention to describe a heart pacemaker which makes possible a mode of operation which is adapted to the physiology, is simple and trouble-free.

SUMMARY OF THE INVENTION

According to the present invention this problem is solved by a pacemaker to which an oxygen measuring electrode is connected. A control unit senses the potential between the charged oxygen electrode and either the stimulating electrode or a reference electrode and utilizes the measuring oxygen level to set a desired heart rate with appropriate outputs then provided to the pacemaker so that the stimulating electrode is stimulated at the desired rate.

In a first embodiment of the device according to the present invention, the $O_2$ measuring electrode is always loaded by a stimulating pulse in parallel with the stimulating electrode. In each instance, prior to the next loading of the $O_2$ measuring electrode (and of the stimulating electrode) the potential of the $O_2$ measuring electrode is measured referred to a reference electrode. The measured potential corresponds to the oxygen concentration of the blood or the heart muscle tissue. An electronic processing circuit assigns to each potential of the $O_2$ measuring electrode, an oxygen concentration level and regulates the frequency, i.e., the number of beats per minute of the heart, as an inverse function of oxygen concentration. Thus, a heart pacemaker with an implantable oxygen sensor which makes possible a mode of operation adapted to the physiology is obtained.

The invention also includes a method for physiological frequency control of heart pacemaker device having a stimulating electrode, a heart pacemaker and an oxygen level measuring electrode connected in parallel and coupled to the heart pacemaker. The method comprises the steps of placing the oxygen level measuring electrode in the blood or the body tissue, loading the oxygen level measuring electrode in the stimulating electrode with stimulating voltage pulses at a variable frequency, measuring the potential of the oxygen level measuring electrode relative to the stimulating electrode between stimulating voltage pulses and controlling the stimulating voltage pulse frequency of the pacemaker as an inverse function of the measured potential.

In a second embodiment of the device according to the present invention, the $O_2$ measuring electrode is likewise loaded in parallel with the stimulating electrode by a stimulating pulse. In this case, however, the potential difference between the $O_2$ measuring electrode and the stimulating electrode prior to the next loading of the $O_2$ measuring electrode is sensed. The $O_2$ measuring electrode preferably is comprised of smooth vitreous carbon and the stimulating electrode preferably of activated vitreous carbon. Such a stimulating electrode has a large double-layer capacity, which results in low polarization. If the oxygen concentrations in the blood or the tissue change quickly, the stimulating electrode of activated vitreous carbon maintains its potential, but the $O_2$ measuring electrode of smooth vitreous carbon changes its potential as a function of the oxygen concentration. By forming the difference of the potentials, possible influences which may become active for both electrodes, of substances of the body, the concentrations of which change more slowly than those of the oxygen, are eliminated. Thus, oxygen concentrations in the blood or the tissue which change quickly can be measured and the frequency of the heart pacemaker can be controlled accordingly.

In the device according to the present invention, the heart pacemaker and the control unit advantageously form a common structural unit. In addition, the lines of the $O_2$ measuring electrode and of the reference electrode can be arranged together with the line of the stimulating electrode in an electrode cable. In this manner, a physiologically controlled heart pacemaker is obtained, the design of which is not appreciably larger than known heart pacemaker designs. Furthermore, the operative intervention does not become more complicated by this design.

BRIEF DESCRIPTION OF THE DRAWINGS

FIG. 1A is a partial block diagram showing an alternative to the embodiment of FIG. 1.

DETAILED DESCRIPTION

Figure 1:
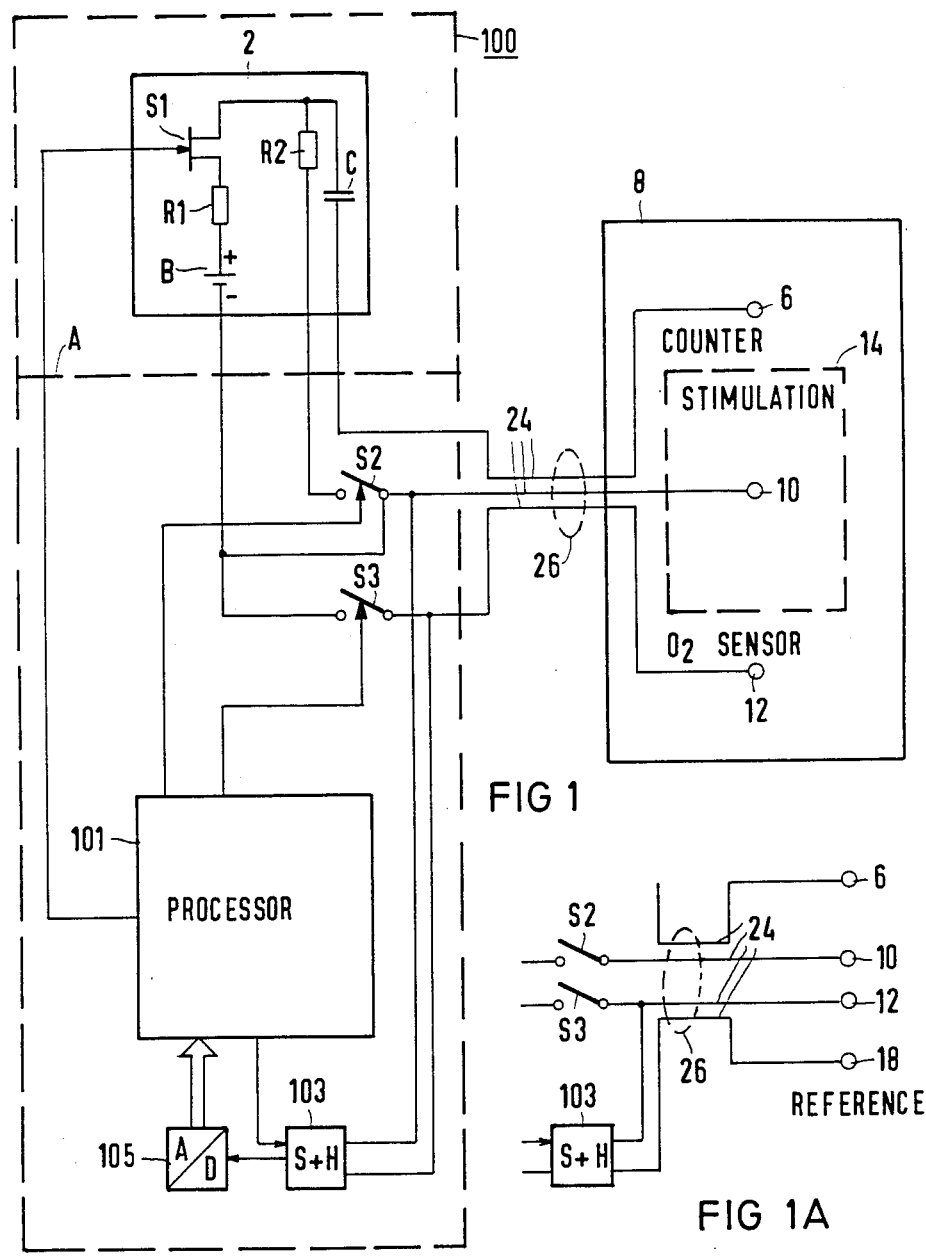
FIG. 1 is a block diagram of a device according to the present invention.

FIG. 1 illustrates the device of the present invention which is generally indicated by the elements within the dotted block 100. Included is a heart pacemaker 2 of conventional design and a control unit 4. Within the control unit 4 is a processor 101, a sample and hold circuit 103, an analog to digital converter 105, and switches indicated as S2 and S3. Associated with the pacemaker is a counter electrode 6 and a stimulating electrode 10 each at the end of a line 24. These are both connected to the patient's body 8, the stimulating electrode being arranged in the heart muscle tissue 14. Also provided is an oxygen sensor electrode or measuring electrode 12 which is also disposed in body 8 or heart muscle tissue 14. All three lines 24 can be formed into a single cable 26. In the embodiment of FIG. 1 the stimulating electrode 10 and oxygen measuring electrode 12 are coupled as inputs to the sample and hold circuit. In the alternative embodiment of FIG. 1A, there is also provided a reference electrode 18 at the end of a line 24 in cable 26 which is also inserted in the body tissue. In that case, it is the reference electrode 18 and the oxygen electrode 12 which are provided as inputs to the sample and hold circuit 103. The stimulating electrode 10 is coupled to an output of the pacemaker 2 through switch S2. Similarly, the oxygen electrode is coupled to the pacemaker through switch S3.

Figure 3:
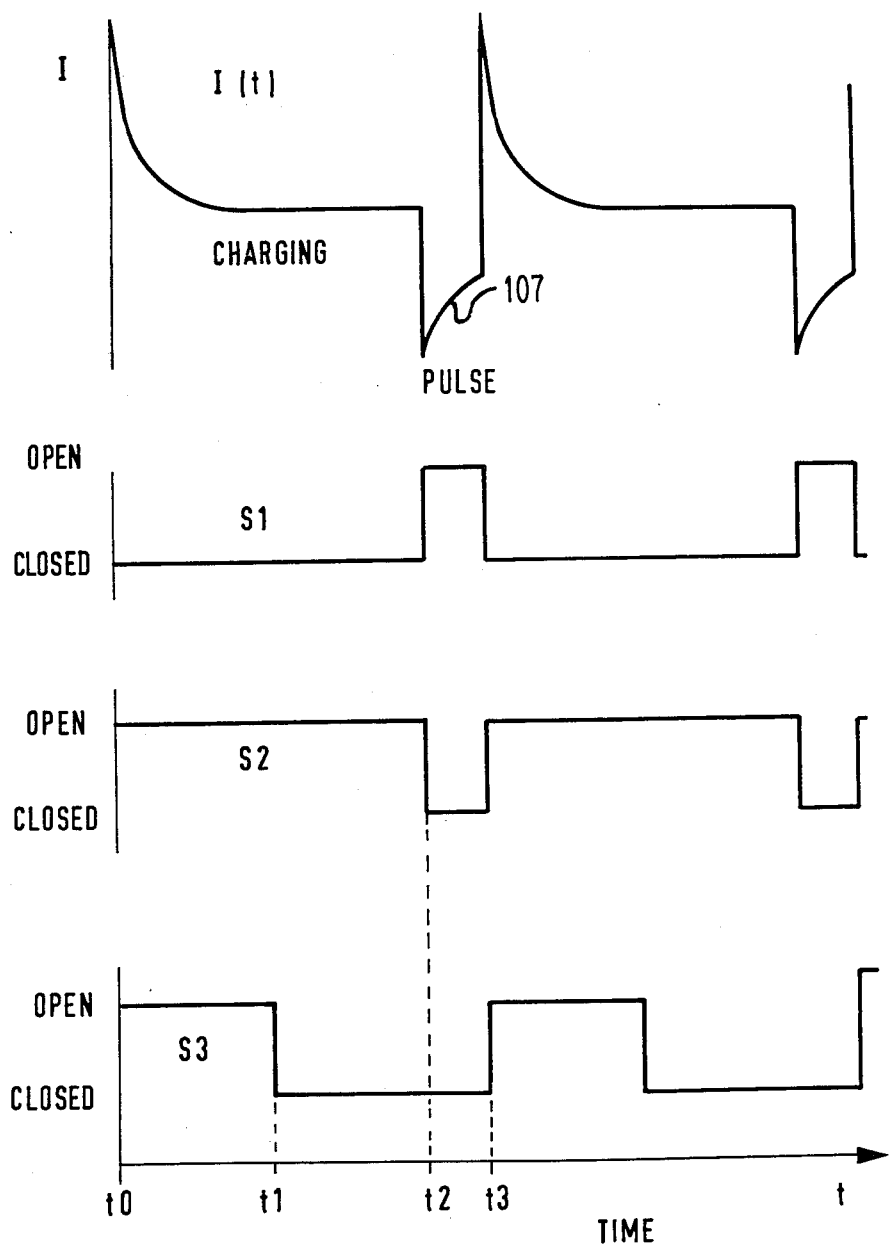
FIG. 3 is a wave form diagram for the device according to FIG. 1.

In operation, as shown in FIG. 3, during a first time period between $t_0$ and $t_2$, a switch S1 in the pacemaker 2 is closed to allow a capacitor C within the pacemaker to charge from a battery B through a resistor R1. The upper curve of FIG. 3 illustrates the capacitor current which will initially be high and then drop off as the capacitor becomes fully charged. After the capacitor is charged, at an appropriate time $t_2$, an output from the processor 101 opens switch S1 and closes the switch S2 to provide a stimulating pulse 107 to the stimulating electrode 10. This is conventional operation in the pacemaker. However, as illustrated by FIG. 3, switch S3, which was closed at time $t_1$, is still closed at this time. Thus, the oxygen electrode 12 is also provided with the stimulating pulse.

The oxygen measuring electrode 12 preferably consists of smooth vitreous carbon, and the stimulating electrode 10 consists preferably of activated vitreous carbon. Although various shapes are possible, preferably both of these electrodes have a hemispheric shape. During the stimulating pulse, low current also initially flows through the oxygen measuring electrode 12. The small amount of current is due to the smooth surface and very low capacitance of electrode 12. This low current is however sufficient for measurement without adversely affecting stimulation.

In operation, the stimulating electrode 10 and the oxygen measuring electrode 12 are thus loaded in parallel by the cathodic stimulating pulses of the heart pacemaker 2. After this stimulation, and after the switch S2 has been opened and the switch S3 opened, at time $t_3$, the processor 101 directs the sample and hold circuit 103 to take a sample of the voltage between the stimulating electrode 10 and the oxygen sensor 12 or alternatively in the case of FIG. 1A between the sensor electrode 12 and the reference electrode 18. This is done between stimulating pulses, i.e., before the next stimulating pulse loads the oxygen measuring electrode 12. The time interval during which the potential of the oxygen measuring electrode can be measured is, for example, 0.5 to 1 msec. Within this time span the potential of the oxygen measuring electrode 12 is at least approximately constant. In accordance with stored data which comprises a digitized form of the curves of FIG. 2 to be explained below, the microprocessor 101 assigns a pulse rate based on the measured potential.

Figure 4:
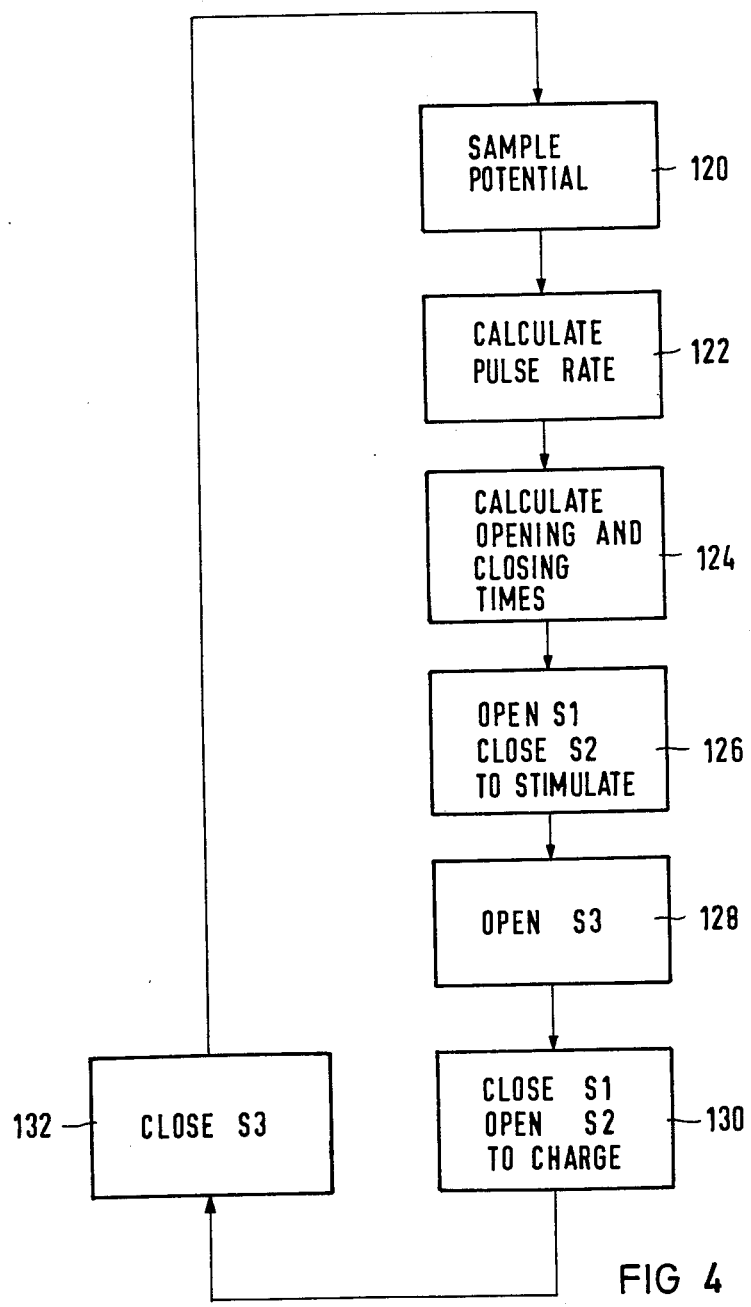
FIG. 4 is a flow diagram of the program in the processor of FIG. 1.

The flow of the program in the processor 101 is illustrated by FIG. 4. As indicated, the potential is sampled by providing an output to sample and hold circuit 103 as indicated by block 120. For this sampled potential, as indicated by block 122 a pulse rate is calculated using stored data. The pulse rate is then used, as indicated in block 124, to calculate opening and closing times for the switches. The nature of the data stored and from which the pulse rate is calculated is that with increasing oxygen concentration in the blood, the number of beats per minute of the pacemaker 2 drops. Conversely, with decreasing oxygen concentration in the blood, the rate of the pacemaker is increased. Once the opening and closing times are calculated, in accordance with block 124, the program can then cause the opening and closing of the switches as indicated by FIG. 3. During the sampling, S1 was closed to allow charging. Now using the calculated pulse time, switch S1 is opened and switch S2 closed to provide an output to the stimulating electrode and to the oxygen electrode. This is shown by block 126. As shown by block 128, switch S3 is then opened and, as indicated by block 130, S1 is closed and S2 opened to carry out charging. Thereafter, switch S3 is again closed as indicated by block 132. Switch S3 is closed during a portion of the charging in order to avoid potential drift of the sensor electrode. The program then loops back to block 120.

Figure 2:
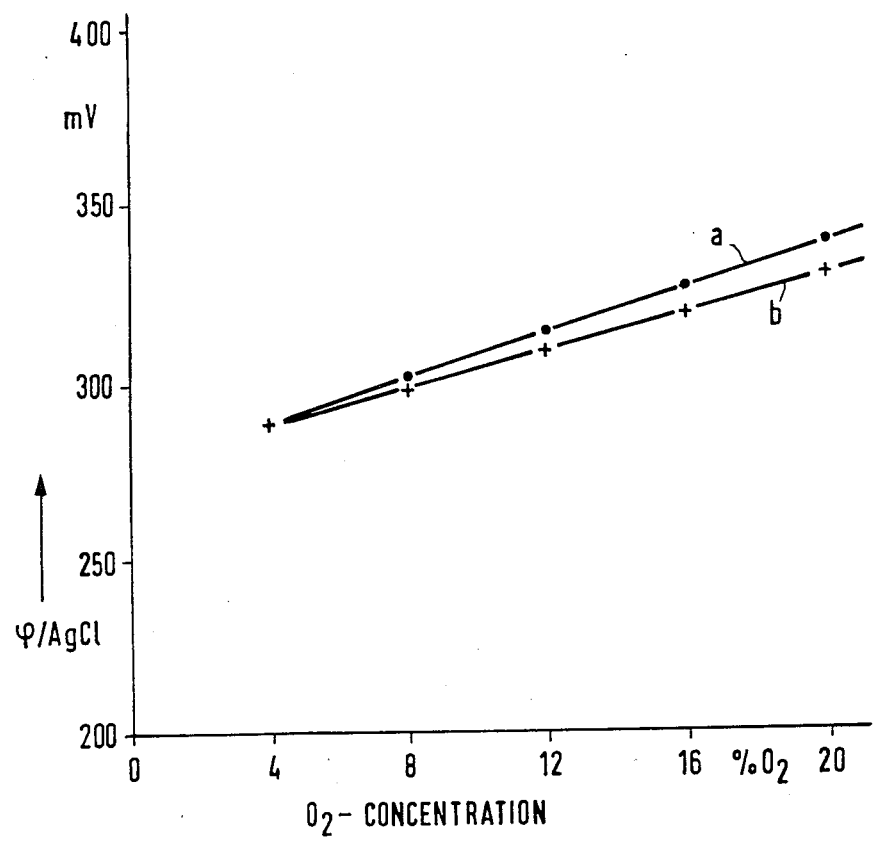
FIG. 2 illustrates calibration curves for the oxygen sensor of FIG. 1.

In the calibration curves according to FIG. 2, the potential φ/AgCl of the O₂ measuring electrode 1 is plotted versus the oxygen concentration. A straight line a with positive slope represents the course of the potential of the O₂ measuring electrode 12 in an electrolyte which is loaded with cathodic stimulating pulses of, for instance, 5V and a pulse length of about 0.5 msec. This electrolyte contains, for instance, 0.9% sodium chloride (NaCl) and, for instance, 0.1% sodium hydrogen carbonate (NaHCO₃) and forms the base electrolyte. A straight line b with positive slope likewise represents the course of the potential of the O₂ measuring electrode 12. There, however, physiological substances such as glucose, urea and amino acid mixtures at their physiologically maximal concentration were added to the base electrolyte. The straight line a and b always start from the same origin but have different slopes. The straight line b, for instance, has a slope of about 50 mV/20% oxygen. The straight line b, which does not deviate substantially from the straight line a, shows that the oxygen concentration can be measured by this measuring method in vivo over an extended period of time in blood or tissue even in the presence of accompanying physiological substances.

What is claimed is:

1. A method for physiological frequency control of a heart pacemaker device having a heart pacemaker, a stimulating electrode having active vitreous carbon and an oxygen level measuring electrode having smooth vitreous carbon connected in parallel and coupled to the heart pacemaker comprising:
   (a) placing the oxygen level measuring electrode in at least one of the blood and the body tissue;
   (b) loading said oxygen level measuring electrode and the stimulating electrode with stimulating voltage pulses at a variable frequency;
   (c) measuring the potential of the oxygen level measuring electrode relative to the stimulating electrode between stimulating voltage pulses; and
   (d) controlling the stimulating voltage pulse frequency of said pacemaker as an inverse function of the measured potential.

2. A method according to claim 1, further comprising the steps of connecting a reference electrode in parallel with the stimulating electrode and the oxygen level measuring electrode and connected to the heart pacemaker;
   in the potential measuring step, measuring the potential of the oxygen level measuring electrode relative to the reference electrode between stimulating voltage pulses.

3. A heart pacemaker device for controlling the physiological frequency of the heart including:
   (a) a heart pacemaker;
   (b) an oxygen level measuring electrode coupled to the pacemaker, wherein said oxygen level measuring electrode comprises smooth vitreous carbon;
   (c) a stimulating electrode coupled to the pacemaker for transmitting stimulating voltage pulses at a variable frequency, wherein said stimulating electrode comprises activated vitreous carbon;
   (d) a counter electrode coupled to the pacemaker;
   (e) means for measuring a potential difference present between the oxygen level measuring electrode and the stimulating electrode responsive to the transmission of a stimulating voltage pulse;
   (f) means for controlling the variable frequency of transmission of stimulating voltage pulses as an inverse function of the sensed potential; and
   (g) means for generating said voltage pulses.

4. A heart pacemaker device according to claim 3 wherein said means for controlling comprises a processing circuit and electronic switch means actuated by the processing circuit for switchably coupling an output of said pacemaker to at least one of said electrodes.

5. A heart pacemaker device according to claim 4, the electronic switch means comprising a first switch coupling the output of said pacemaker to the stimulating electrode and a second switch for coupling the output of said pacemaker to said oxygen level measuring electrode and wherein said means for controlling is adapted to close both of said switches during the generation of a stimulating pulse.

6. A heart pacemaker device according to claim 5 wherein said processing circuit comprises a processor controlling the operation of said switches.

7. A heart pacemaker device for controlling the physiological frequency of the heart including:
   (a) a heart pacemaker;
   (b) an oxygen level measuring electrode coupled to the pacemaker, wherein said oxygen level measuring electrode is a smooth vitreous carbon electrode;
   (c) a stimulating electrode coupled to the pacemaker for transmitting stimulating voltage pulses at a variable frequency, wherein said stimulating electrode is an activated vitreous carbon electrode;
   (d) an additional electrode coupled to the pacemaker for measuring a reference potential;
   (e) a counter electrode coupled to the pacemaker;
   (f) means for measuring a potential difference present between the oxygen level measuring electrode and the additional electrode responsive to the transmission of a stimulating voltage pulse;
   (g) means for controlling the variable frequency of transmission of stimulating voltage pulses as an inverse function of the measured potential; and
   (h) means for generating said voltage pulses.

8. A heart pacemaker device according to claim 7 wherein said means for controlling comprises a processing circuit and electronic switch means actuated by the processing circuit for switchably coupling an output of said pacemaker to at least one of said electrodes.

9. A heart pacemaker device according to claim 8, the electronic switch means comprising a first switch coupling the output of said pacemaker to the stimulating electrode and a second switch for coupling the output of said pacemaker to said oxygen level measuring electrode and wherein said means for controlling is adapted to close both of said switches during the generation of a stimulating pulse.

10. A heart pacemaker device according to claim 9 wherein said processing circuit comprises a processor controlling the operation of said switches.

* * * * *